United States Patent

Kerkmann et al.

Patent Number: 6,018,165
Date of Patent: Jan. 25, 2000

[54] OPTOELECTRONIC SENSOR DEVICE

[75] Inventors: Detlef Kerkmann, Nachrodt; Berthold Esders, Schalksmühle; Ralf Böbel, Dortmund, all of Germany

[73] Assignee: Leopold Kostal GmbH & Co. KG, Ludenscheid, Germany

[21] Appl. No.: 09/039,791

[22] Filed: Mar. 16, 1998

[30] Foreign Application Priority Data

Apr. 2, 1997 [DE] Germany .............................. 197 13 910

[51] Int. Cl.⁷ ...................................................... G02B 6/42
[52] U.S. Cl. ...................... 250/574; 250/227.25; 318/483
[58] Field of Search ................................ 250/574, 227.25, 250/216, 341.8; 318/483, DIG. 2; 340/602

[56] References Cited

U.S. PATENT DOCUMENTS 5,818,600  10/1998  Bendicks et al. ................. 250/227.25

Primary Examiner—Edward P. Westin
Assistant Examiner—Kevin Pyo
Attorney, Agent, or Firm—Brooks & Kushman PC

[57] ABSTRACT

An optoelectronic sensor device for detecting precipitation on an outer surface (41) of a transparent pane (4) of a motor vehicle includes a beam guide element (1) having front and rear opposed parallel surfaces (2, 7) and first and second lateral opposed faces (5, 6). The front surface (2) is coupled to an inner surface (42) of a transparent pane (4) of a motor vehicle. Each of the lateral faces (5, 6) has a reflection region (52, 62). The rear surface (7) has first and second cut-out portions (8, 81) extending therefrom toward the front surface (2). Each of the cut-out portions (8, 81) has a reflective region (11). A beam transmitter (13) is disposed adjacent the rear surface (7) to transmit an infrared beam to the reflective region (11) of the first cut-out portion (8). The reflective region (11) of the first cut-out portion (8) reflects a beam transmitted from the beam transmitter (13) to the reflection region (52) of the first lateral face (5) which reflects the beam to the transparent pane (4). The transparent pane (4) reflects a part of the beam to the reflection region (62) of the second lateral face (6). The part of the beam reflected by the transparent pane (4) is a function of the precipitation on the outer surface (41) of the transparent pane (4). A beam receiver (14) is disposed adjacent the rear surface (7) to receive an infrared beam from the reflective region (62) of the second cut-out portion (81). The second lateral face (62) reflects the part of the beam reflected by the transparent pane (4) to the second cut-out portion (81) which reflects the part of the beam to the beam receiver (14).

9 Claims, 1 Drawing Sheet

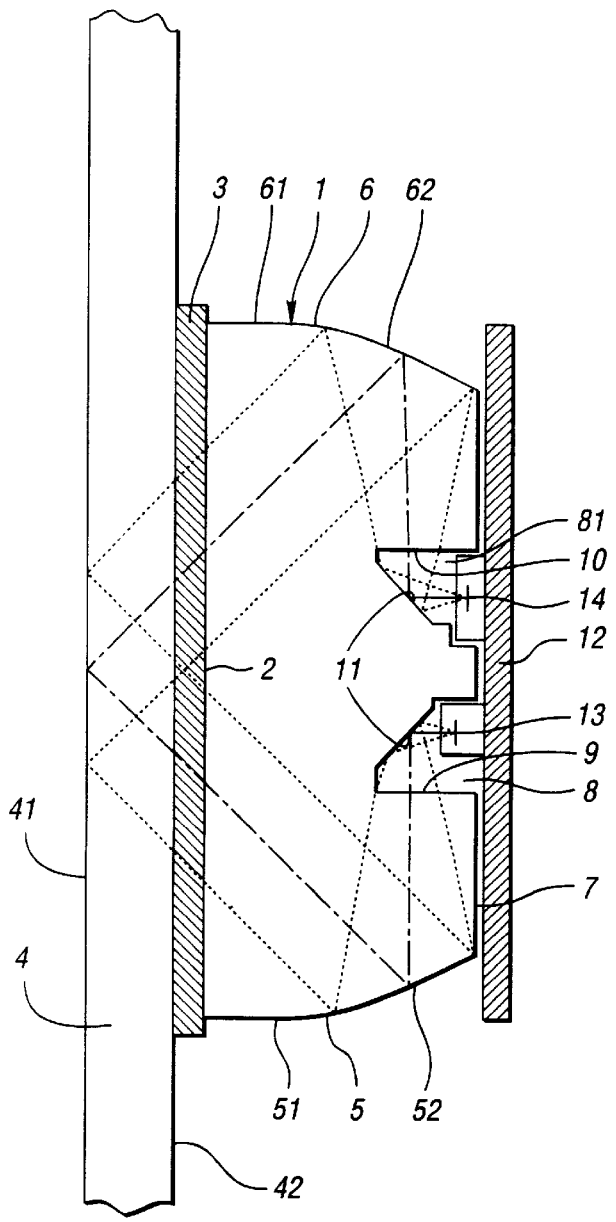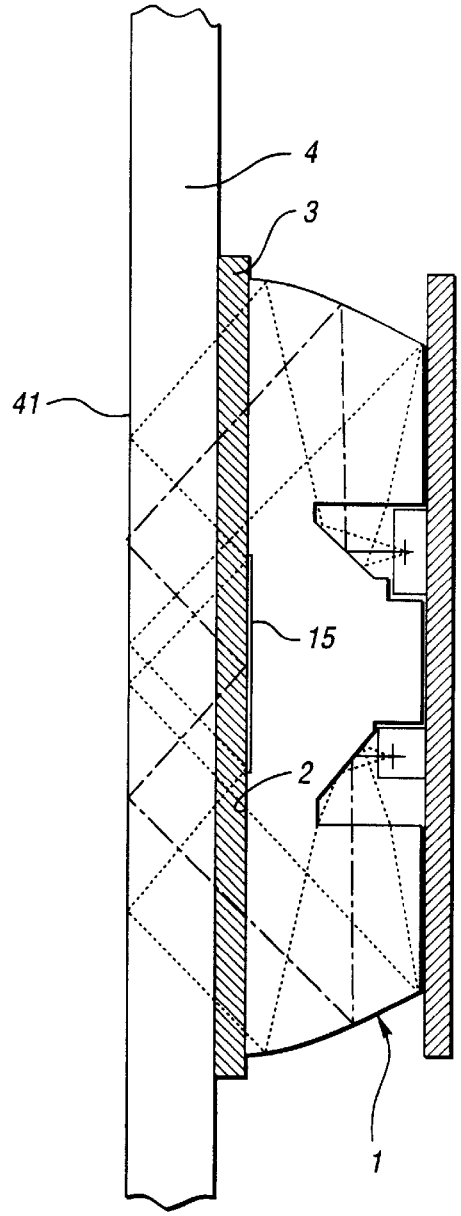

OPTOELECTRONIC SENSOR DEVICE

TECHNICAL FIELD

The present invention relates to an optoelectronic sensor device for detecting precipitation on a transparent pane of a motor vehicle.

BACKGROUND ART

Prior art optoelectronic sensors devices for detecting precipitation on a transparent pane of a motor vehicle include a beam guide element. The beam guide element has a beam transmitter and a beam receiver. The beam transmitter transmits a beam to the pane. The beam transmitter includes a parallelizing component to cause the beam to propagate as an in-phase beam wavefront. A part of the beam transmitted to the pane passes through the pane into the outside environment. Another part of the beam transmitted to the pane is reflected by the pane. The reflection proportion is dependent upon the amount of precipitation on the pane. The reflected beam is then received by a beam receiver. The beam receiver includes a focusing component for focusing the reflected beam from the pane to the beam receiver. A problem with the prior art optoelectronic sensors is that the parallelizing and focusing components require a considerable length of installation space in addition to the space required by the beam guide element.

SUMMARY OF THE INVENTION

Accordingly, it is an object of the present invention is to provide an optoelectronic precipitation detecting sensor device having a minimal number of optical components, reduced installation length, and improved optical characteristics.

It is another object of the present invention to provide an optoelectronic precipitation detecting sensor device having a beam guide element which parallelizes and focuses beams without separate parallelizing and focusing components, thereby enabling the device to be reduced in size.

It is a further object of the present invention to provide an optoelectronic precipitation detecting sensor device having a beam guide element with a pair of parabolic lateral faces for obtaining improved optical characteristics.

In carrying out the above objects and other objects, the present invention provides an optoelectronic sensor device for detecting precipitation on an outer surface of a transparent pane of a motor vehicle. The sensor device includes a beam guide element having front and rear opposed parallel surfaces and first and second lateral opposed faces. The front surface is coupled to an inner surface of a transparent pane of a motor vehicle. Each of the lateral faces has a reflection region. The rear surface has first and second cut-out portions extending therefrom toward the front surface. Each of the cut-out portions has a reflective region.

A beam transmitter is disposed adjacent the rear surface of the beam guide element within the first cut-out portion to transmit an infrared beam toward the reflective region of the first cut-out portion. The reflective region of the first cut-out portion reflects a beam transmitted from the beam transmitter to the reflection region of the first lateral face which reflects the beam to the transparent pane. The transparent pane reflects a part of the beam to the reflection region of the second lateral face. The part of the beam reflected by the transparent pane is a function of the precipitation on the outer surface of the transparent pane.

A beam receiver is disposed adjacent the rear surface of the beam guide element within the second cut-out portion to receive an infrared beam from the reflective region of the second cut-out portion. The second lateral face reflects the part of the beam reflected by the transparent pane to the second cut-out portion which reflects the part of the beam to the beam receiver.

These and other features, aspects, and embodiments of the present invention will become better understood with regard to the following description, appended claims, and accompanying drawings.

BRIEF DESCRIPTION OF THE DRAWINGS

FIG. 1 illustrates a cross-sectional view of a sensor device in accordance with a first embodiment of the present invention; and FIG. 2 illustrates a cross-sectional view of a sensor device in accordance with a second embodiment of the present invention.

BEST MODE FOR CARRYING OUT THE INVENTION

Referring now to FIG. 1, a cross-sectional view of an optoelectronic sensor device in accordance with a preferred embodiment of the present invention is shown. The sensor device includes a beam guide element 1. Beam guide element 1 has a substantially planar front surface 2. Front surface 2 is bonded by means of an optically transparent layer 3, e.g., an adhesive layer, to an inner surface 42 of a transparent motor vehicle pane 4, e.g., the front pane of a motor vehicle. Pane 4 includes an outer surface 41 which becomes wet when it is raining. The sensor device is operable to measure the degree of wetting of outer surface 41 of pane 4.

Front surface 2 of beam guide element 1 is adjoined by substantially vertically aligned opposed first and second lateral faces 5 and 6. Lateral faces 5 and 6 include non-metallized lateral opposed parallel face portions 51 and 61, respectively, and reflection regions 52 and 62. Face portions 51 and 61 extend from front surface 2 perpendicular thereto. Reflection regions 52 and 62 are metallized and have a parabolic shape to reflect and focus infrared beams.

Beam guide element 1 also includes a rear surface 7 opposed from and aligned in parallel with front surface 2. Rear surface 7 includes first and second cut-out portions 8 and 81 extending therefrom toward front surface 2. Cut-out portions 8 and 81 have a trapezoidal cross-section and are mirror images of one another. Cut-out portion 8 includes a transparent beam entry face 9 and a reflective base region 11. Beam entry face 9 is aligned perpendicular to front surface 2. Reflective region 11 of cut-out portion 8 extends at an angle of approximately 45° with respect to beam entry face 9. Similarly, cut-out portion 81 includes a transparent beam exit face 10 and a reflective base region 11. Beam exit face 10 is aligned perpendicular to front surface 2. Reflective region 11 of cut-out portion 81 extends at an angle of approximately 45° with respect to beam exit face 10.

A planar substrate 12 is positioned adjacent rear surface 7 of beam guide element 1. Substrate 12 is a printed circuit board held to rear surface 7 by associated components. A beam transmitter 13 and a beam receiver 14 are disposed on substrate 12. Beam transmitter 13 is an infrared beam transmit diode and beam receiver 14 is an infrared beam receive diode. Beam transmitter 13 and beam receiver 14 are integrated directly into substrate 12.

Beam transmitter 13 is disposed on substrate 12 adjacent rear surface 7 within cut-out portion 8 to transmit an infrared beam toward reflective region 11 of cut-out portion 8. Similarly, beam receiver 14 is disposed on substrate 12 adjacent rear surface 7 within cut-out portion 81 to receive an infrared beam from reflective region 11 of cut-out portion 81.

The operation of the optoelectronic sensor device will now be described. Initially, beam transmitter 13 transmits an infrared beam to reflective region 11 of cut-out portion 8. The transmitted beam is a divergent light beam bundle. Reflective region 11 of cut-out portion 8 then reflects the divergent beam bundle through beam entry face 9 to reflection region 52. Reflection region 52 causes the divergent beam bundle to be reflected and propagated to pane 4 as an in-phase beam wavefront. Reflection region 52 is operable with reflective region 11 of cut-out portion 8 such that the in-phase beam wavefront passes into pane 4 at an angle of approximately 45°.

At outer surface 41 of pane 4, part of the beam passes through the outer surface into the environment and another part of the beam is reflected to reflection region 62. The proportion of the beam reflected by outer surface 41 to the beam passing through the outer surface is a function of the amount of precipitation on the outer surface. Accordingly, the optoelectronic sensor measures the beam reflected by outer surface 41 to determine the amount of precipitation on the outer surface.

Reflection region 62 reflects and focuses the part of the beam reflected by outer surface 41 through beam exit face 11 to converge on reflective region 11 of cut-out portion 81. Reflective region 11 of cut-out portion 81 then reflects the beam part to beam receiver 14. As mentioned above, the magnitude of the beam part received by beam receiver 14 is indicative of the amount of precipitation on outer surface 41 of pane 4.

Referring now to FIG. 2, a cross-sectional view of a sensor device in accordance with a second embodiment of the present invention is shown. Beam guide element 1 shown in FIG. 2 includes many of the same elements as the beam guide element shown in FIG. 1. Front surface 2 of beam guide element 1 of FIG. 2 includes a metallized central region 15. Central region 15 intercepts and reflects the beam reflected from outer surface 41 of pane 4 back to the outer surface. A part of the intercepted beam reflected from central region 15 then passes through pane 4 into the outside environment and another part of the intercepted beam is then reflected from outer surface 41 to the reflection region of the lateral face associated with the beam receiver. Because of the reflection provided by central region 15 the travel path of the beam reflected between outer surface 41 and the lateral faces is reduced. Thus, each of the lateral faces do not include the lateral opposed parallel face portions. As a result, the volume taken up by the beam guide element of FIG. 2 is reduced from the volume taken up by beam the beam guide element of FIG. 1.

Thus it is apparent that there has been provided, in accordance with the present invention, a sensor device for detecting precipitation on a transparent pane of a motor vehicle that fully satisfies the objects, aims, and advantages set forth above.

While the present invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

What is claimed is:

1. An optoelectronic sensor device for detecting precipitation on an outer surface of a transparent pane of a motor vehicle, the sensor device comprising:

a beam guide element having front and rear opposed parallel surfaces and first and second lateral opposed faces, the front surface coupled to an inner surface of a transparent pane of a motor vehicle, each of the lateral faces having a reflection region, the rear surface having first and second cut-out portions extending therefrom toward the front surface, each of the cut-out portions having a reflective region;

a beam transmitter disposed adjacent the rear surface of the beam guide element within the first cut-out portion to transmit an infrared beam toward the reflective region of the first cut-out portion, wherein the reflective region of the first cut-out portion reflects a beam transmitted from the beam transmitter to the reflection region of the first lateral face which reflects the beam to the transparent pane, wherein the transparent pane reflects a part of the beam to the reflection region of the second lateral face, wherein the part of the beam reflected by the transparent pane is a function of the precipitation on the outer surface of the transparent pane; and a beam receiver disposed adjacent the rear surface of the beam guide element within the second cut-out portion to receive an infrared beam from the reflective region of the second cut-out portion, wherein the second lateral face reflects the part of the beam reflected by the transparent pane to the second cut-out portion which reflects the part of the beam to the beam receiver.

2. The sensor device of claim 1 wherein:

the reflection regions of the first and second lateral faces have parabolic shapes.

3. The sensor device of claim 2 wherein:

the first and second lateral faces include respective first and second lateral opposed parallel face portions extending from the front surface of the beam guide element perpendicular thereto.

4. The sensor device of claim 1 wherein:

the reflective regions of the cut-out portions are metallized.

5. The sensor device of claim 1 wherein:

the first and second cut-out portions include beam entry and beam exit faces, respectively, aligned perpendicular to the front surface of the beam guide element.

6. The sensor device of claim 5 wherein:

the beam transmitter and the beam receiver are each aligned with the reflective region of the first and second cut-out portions, respectively, wherein the first and second reflective regions extend at an angle of approximately 45° with respect to the beam entry and beam exit faces.

7. The sensor of claim 1 further comprising:

a planar substrate adjacent the rear surface of the beam guide element, wherein the beam transmitter and the beam receiver are disposed on the planar substrate.

8. The sensor device of claim 7 wherein:

the substrate is a printed circuit board.

9. The sensor device of claim 1 wherein:

the front surface of the beam guide element includes a metallized central region.

\* \* \* \* \*